United States Patent [19]
Loibner et al.

[11] Patent Number: 5,523,085
[45] Date of Patent: Jun. 4, 1996

[54] MONOCLONAL ANTIBODY IN DESTRUCTION OF SMALL CELL LUNG CARCINOMA

[75] Inventors: Hans Loibner; Dieter Scholz, both of Vienna, Austria

[73] Assignee: Sandoz Ltd., Basel, Switzerland

[21] Appl. No.: 378,890

[22] Filed: Jan. 24, 1995

Related U.S. Application Data

[63] Continuation of Ser. No. 93,416, Jul. 19, 1993, abandoned, which is a continuation of Ser. No. 661,745, Feb. 27, 1991, abandoned.

[30] Foreign Application Priority Data

Feb. 28, 1990 [DE] Germany ................. 40 06 308.9

[51] Int. Cl.$^6$ ............... A61K 39/395; C07K 16/18; C07K 16/30
[52] U.S. Cl. ............... 424/137.1; 424/133.1; 424/174.1; 424/181.1; 424/155.1; 530/388.8; 530/388.85; 530/387.3
[58] Field of Search ............ 530/388.8, 388.85, 530/387.3; 424/155.1, 174.1, 181.1, 133.1, 137.1; 435/240.27

[56] References Cited

FOREIGN PATENT DOCUMENTS 0285059  5/1988  European Pat. Off. .

OTHER PUBLICATIONS

Thom et al, Biochem J., vol. 168, pp. 187–194 (1977).
Laemmli, Nature, vol. 227, pp. 680–685 (1970).
Wilson et al, Immunofluorescence and Related Staining Techniques, Knapp et al—editors, pp. 215–224 (1978).
Colvin, Diagnotic Immunopathology, Raven Press, New York, pp. 437–452 (1988).
Steplewski, Z. et al., Hybridoma, vol. 9(2):201–210, 1990.
Scholz, D. et al., Cancer Immunol Immunother, 33:153–157, 1991.
Waldmann, T., Science, 252:1657–1662, 21 Jun. 1991.
Osband, M. E. et al., Immunology Today, 11(6):193–195, 1990.
Kannagi, R. et al, Handbook of Exp. Immunol, 4:117.1–117.20, May 30, 1986.

*Primary Examiner*—Lila Feisee
*Assistant Examiner*—Susan A. Loring
*Attorney, Agent, or Firm*—Townsend and Townsend and Crew

[57]  ABSTRACT

Monoclonal antibody BR55-2 and fragments thereof having the specificity of monoclonal antibody BR55-2, and variants thereof, are useful in the treatment of small cell lung carcinoma.

10 Claims, 6 Drawing Sheets

MONOCLONAL ANTIBODY IN DESTRUCTION OF SMALL CELL LUNG CARCINOMA

This is a Continuation of application Ser. No. 08/093,416, filed Jul. 19, 1993, now abandoned which is a continuation of application Ser. No. 07/661,745 filed Feb. 27, 1991, now abandoned.

FIELD

The invention relates to a new use of a monoclonal antibody. It concerns the use of a monoclonal antibody BR55-2 or a fragment thereof having the specificity of monoclonal antibody BR55-2, or a variant thereof, in the treatment of small cell lung carcinoma (SCLC).

BACKGROUND

The use of monoclonal antibodies in therapeutic applications is gaining increasing acceptance.

One such group of monoclonal antibodies, of murine origin, is BR55-2 or fragments thereof having the same specificity and their variants, disclosed in e.g. Wistar EP 0 285 059, which also discloses their preparation and their use in the detection and therapy of, basically, adenocarcinomas and similar tumors. The BR55-2 class of antibodies recognizes the difucosyl blood group antigens Y-6 and B-7-2 normally associated with adenocarcinomas.

The etiology of small cell lung carcinoma is rather obscure but unrelated to malignancies of epithelial origin such as adenocarcinomas. Indeed, monoclonal antibodies known to exert an inhibitory effect on the development of adenocarcinomal malignancies are normally without effect on small cell lung carcinoma cells, and vice-versa, while a few monoclonal antibodies have been alleged to recognize both types of cells.

SUMMARY OF THE INVENTION

It has now been found that, surprisingly, the above difucosyl blood group antigens are also present on SCLC cells and the BR55-2 antibodies have an excellent inhibitory activity in small cell lung carcinoma, while not inducing in vivo the production of functionally neutralizing antimurine immunoglobulins.

The invention thus comprises the use of a monoclonal antibody BR55-2 or a fragment thereof having the specificity of monoclonal antibody BR55-2, or a variant thereof, in the treatment of small cell lung carcinoma.

It further comprises the use of a monoclonal antibody BR55-2 or a fragment thereof having the specificity of monoclonal antibody BR55-2, or a variant thereof, for the manufacture of a medicament for the treatment of small cell lung carcinoma.

It further includes a method of treating small cell lung carcinoma comprising administering to a subject in need of such treatment a therapeutically effective amount of a monoclonal antibody BR55-2 or a fragment thereof having the specificity of monoclonal antibody BR55-2, or a variant thereof.

It further comprises a pharmaceutical composition which comprises as active agent a monoclonal antibody BR55-2 or a fragment thereof having the specificity of monoclonal antibody BR55-2, or a variant thereof, together with a pharmaceutically acceptable carrier or diluent, for use in the treatment of small cell lung carcinoma.

It further includes a process for the manufacture of a medicament for use in the treatment of small cell lung carcinoma which comprises mixing a monoclonal antibody BR55-2 or a fragment thereof having the specificity of monoclonal antibody BR55-2, or a variant thereof, with a pharmaceutically acceptable carrier or diluent.

DETAILED EXPLANATION

The new use in SCLC is based on the following findings:

1. Binding studies

1.1. Binding of BR55-2 antibodies to SCLC cell lines

Figure 1:
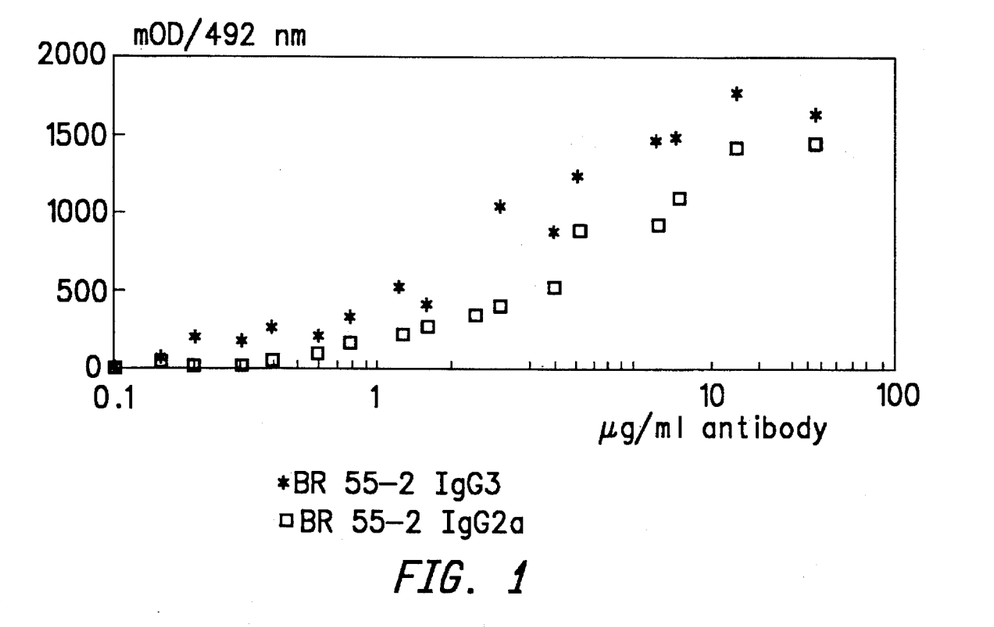
FIG. 1: Binding properties (cell ELISA) of BR55-2 isotypes IgG3 (stars) and IgG2a (open squares) to SCLC cell line SW2.
Figure 2:
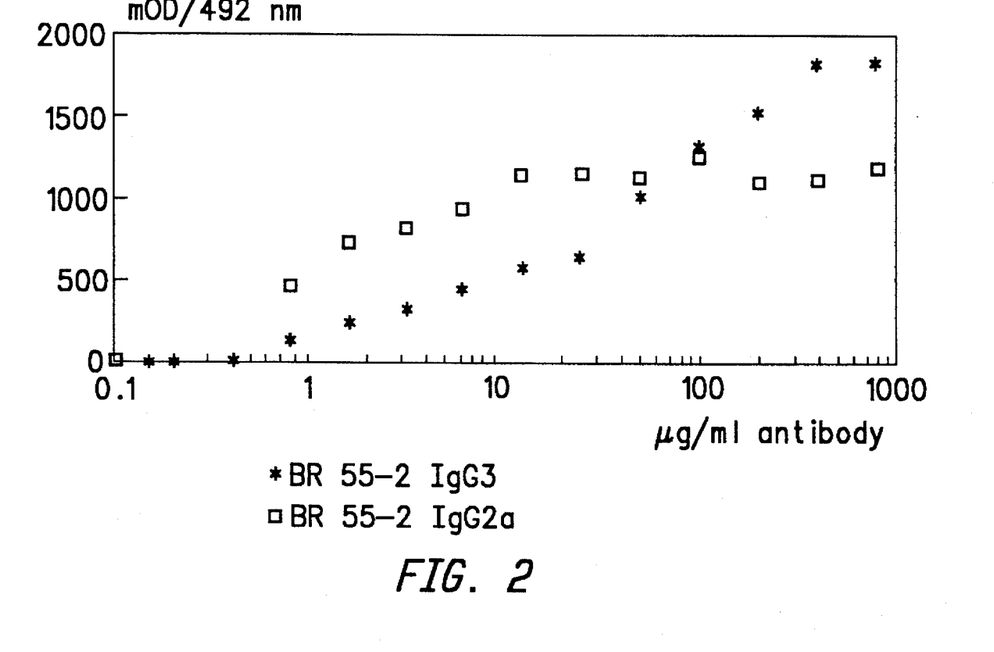
FIG. 2: As for FIG. 1, but with cell line OH-1.
Figure 3:
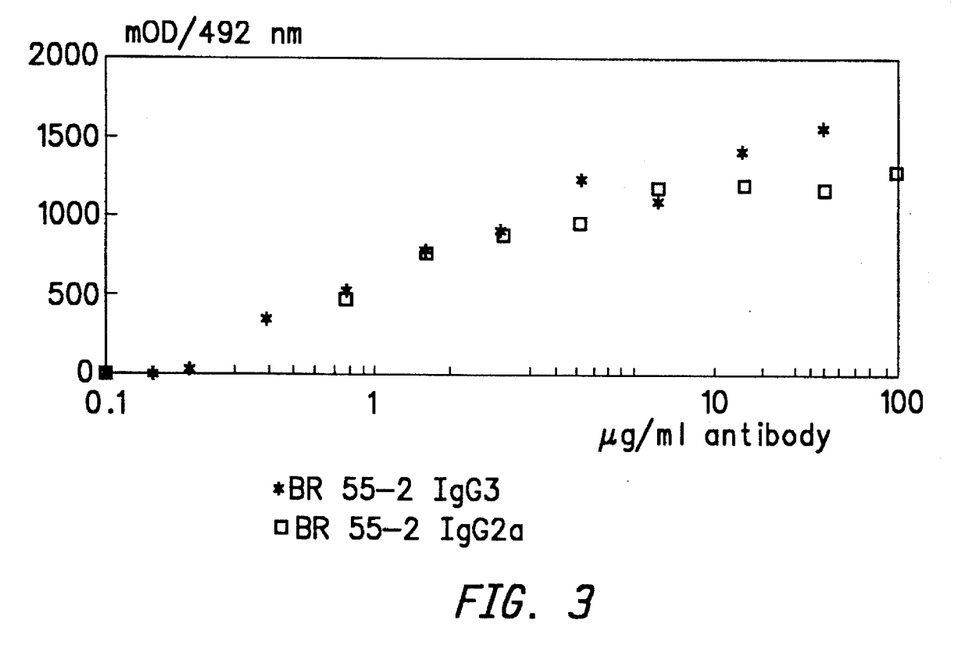
FIG. 3: As for FIG. 1, but with cell line H-69.

The Lewis Y carbohydrate antigen which is defined by antibodies BR55-2 is surprisingly also significantly expressed on SCLC cell lines. This can be shown in binding studies of the BR55-2 antibodies with SCLC cell lines SW2, OH-1 and H-69 in a cell-ELISA (see FIGS. 1, 2 and 3, and Example 1 for experimental details).

Analogous results are also obtained with e.g. SCLC cell lines LX-1, OH-3 and ZTL2 in the Johnstone and Thorpe immunofluorescence assay (*Immunochemistry in Practice*, Blackwell Scientific Publications, Oxford, 1987).

The expression of the Lewis Y carbohydrate antigen on glycoproteins of cell line SW2 can further be demonstrated as described in Example 8.

1.2. Binding of BR55-2 antibodies to human SCLC tissue samples

Binding of the antibodies was investigated on frozen sections from human SCLC using the immunohistochemical method of R. B. Colvin et al., *Diagnostic Immunopathology*, Raven Press, New York (1988). BR55-2 was found to bind strongly on 5 out of 7 investigated samples and somewhat weaker on the remaining 2 samples.

2. Cytolytic and cytotoxic activity on SCLC cell lines in vitro

This effect is mediated via induction of human effector functions. In principle the destruction of tumor cells due to the antibodies can be based on two general mechanisms: complement-dependent cytolysis (CDC) and antibody-dependent cell cytotoxicity (ADCC).

2.1. CDC

After binding to human SCLC cell lines and depending on their isotype, antibodies BR55-2 activate human complement, which in turn destroys tumor cells, as is well-known. The source of the complement to be used in such tests can be human plasma or serum. The destruction of tumor cells can be measured by the release of previously incorporated $^{51}$Cr.

Figure 4:
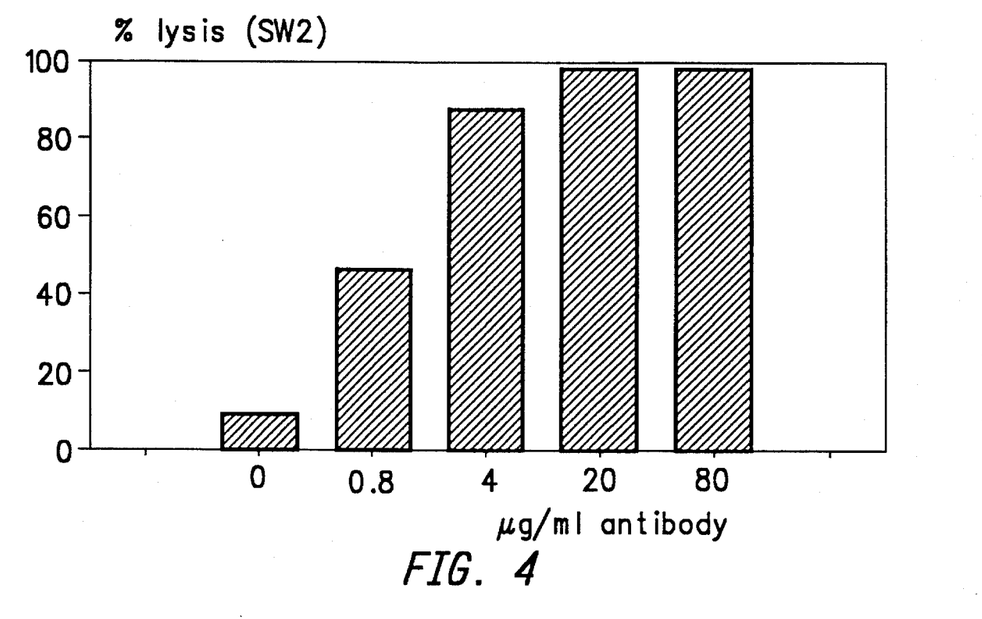
FIG. 4: Complement-dependent cytolysis (CDC) (in % lysis of cells of SCLC cell line SW2) with BR55-2/IgG3.
Figure 5:
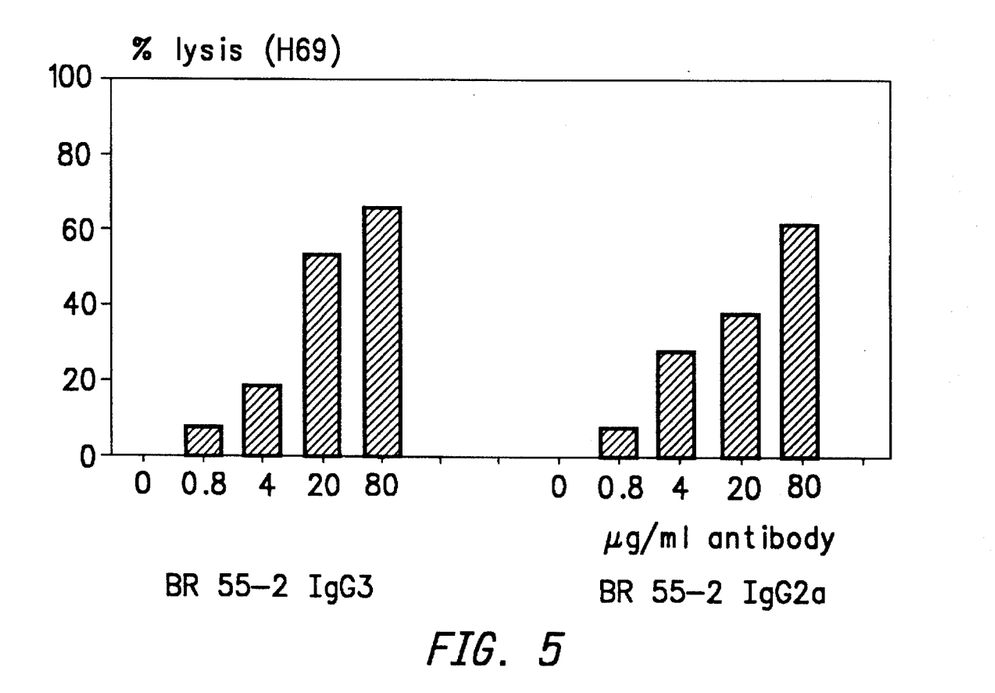

The results from such complement-mediated cytolysis experiments using tumor cell lines SW2 and H-69 are shown in FIGS. 4 and 5 (see Example 2 for experimental details). It can be seen that antibodies BR55-2 have excellent tumoricidal activity mediated by complement activation on these cell lines.

2.2. ADCC

2.2.1. Using peripheral blood mononuclear cells

Depending on their isotype antibodies BR55-2 activate human effector cells for selective destruction-of human SCLC cell lines. These effector cells then destroy the tumor cells, as is well-known. Peripheral blood mononuclear cells (PBMCs) from heparinized fresh human blood for example are a convenient source of human effector cells. Tumor cell destruction can be measured e.g. by the release of preincorporated $^{51}Cr$.

Figure 6:
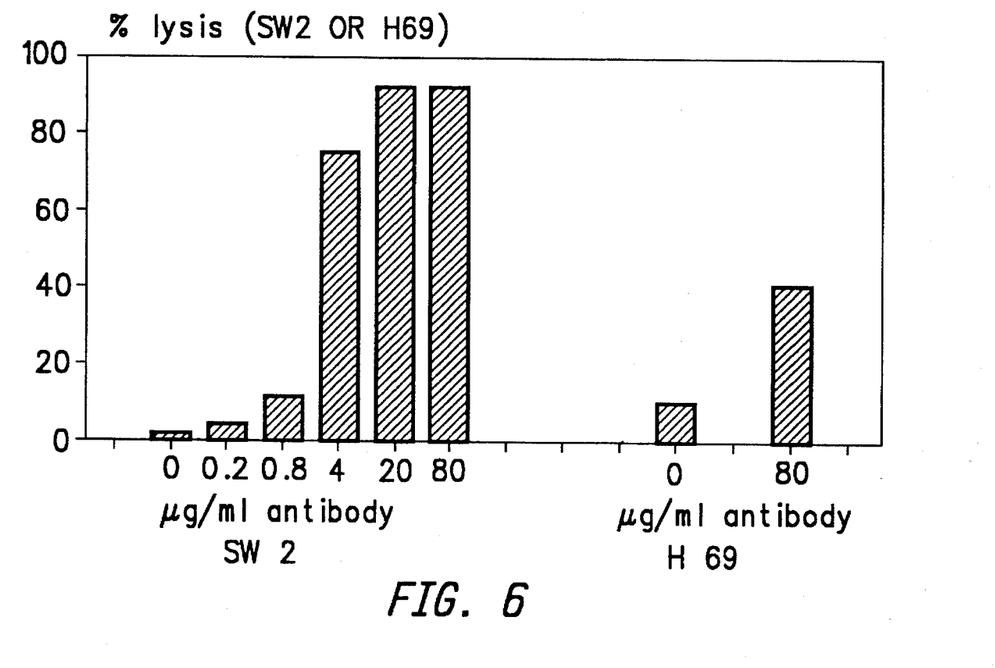
FIG. 6: ADCC (in % lysis of cells) for SCLC cell lines SW2 and H-69 with PBMCs as effector cells, mediated by BR55-2/IgG3.

The results from such experiments are shown in FIG. 6 (see Example 3 for experimental details). It appears therefrom that antibodies BR55-2 are good activators of human effector cells in ADCC.

2.2.2. Using heparinized fresh human whole blood

In the standard experiments described above either human plasma or serum is used as a source of complement, and freshly isolated human PBMCs as effector cells. These conditions are not physiological since the two effector principles are separated. Therefore, lysis of human SCLC cell lines by heparinized human, whole blood was also investigated. Conditions closer to the situation in vivo are created with this combination of both effector mechanisms.

Figure 7:
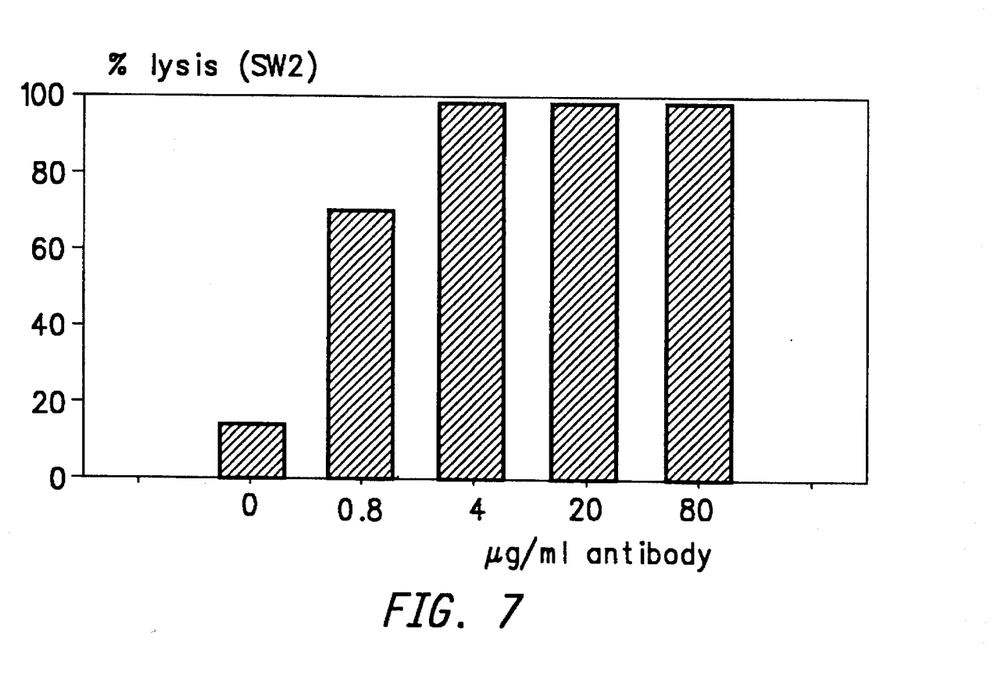
FIG. 7: Lysis of SW2 cells with heparinized fresh human whole blood, mediated by BR55-2/IgG3.

It was found that antibodies BR55-2 are excellent mediators—depending on their isotype—in the destruction of human SCLC cell lines by human whole blood. A representative result of such tests is presented in FIG. 7 (see Example 4 for experimental details). The heparinized whole blood used in these tests originates from a patient with advanced SCLC.

3. Serological results from a clinical trial in SCLC patients

In the course of a Phase-I clinical trial patients with advanced SCLC resistant to chemotherapy were treated with antibody BR55-2/IgG3. In view of the terminal stage of their disease of course no measurable healing effect was to be expected. The patients received antibody over two weeks as a slow intravenous infusion of 50 mg (12 patients) or 100 mg (4 patients) dissolved in saline on each of days 1, 3, 5, 8, 10 and 12. During this 2-weeks period serum samples were submitted to the following assays:

—concentration of BR55-2/IgG3 in the serum;
—capacity of the serum to destroy a SCLC cell line without addition of any further ingredients (CDC by the infused antibody present in the serum);
—human immune response against the administered murine protein.

3.1. Serum antibody titer

Figure 8:
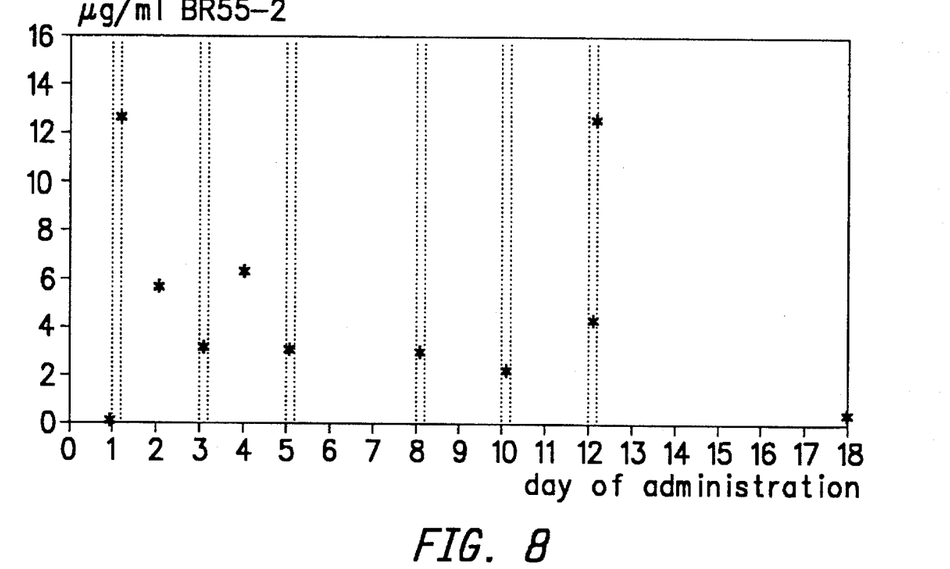
FIG. 8: BR55-2 determination as mouse-IgG3 antibody titer in serum from a SCLC patient: administration was of 50 mg BR55-2/IgG3 on each of days 1, 3, 5, 8, 10 and 12. The interrupted vertical lines show the duration of infusion.

Antibody BR55-2/IgG3 is present in serum at a concentration of several µg/ml after i.v. infusion. Depending on the dosage, the half-life period (on average about 24 hours) and the timepoint after infusion, concentrations of from about 2 µg/ml to about 13 µg/ml can be measured over the whole period of treatment with 50 mg per infusion, as shown in FIG. 8 (see Example 5 for experimental details). The concentrations of antibody in the serum are obviously at their lowest shortly before the next infusion as shown by the preinfusion antibody concentrations of day 1 and 12, which are represented as solid squares in FIG. 8.

Such serum antibody titers can be detected e.g. as mouse-Ig generally (Example 5).

3.2. Ex vivo tumor cytotoxicity of SCLC patient sera for cell line SW2 (CDC)

Serum samples were collected from patients at various times during treatment and tested for cytotoxicity against SCLC cell line SW2. This tumor cell cytotoxicity is caused via complement activation by BR55-2 antibody present in serum.

Figure 9:
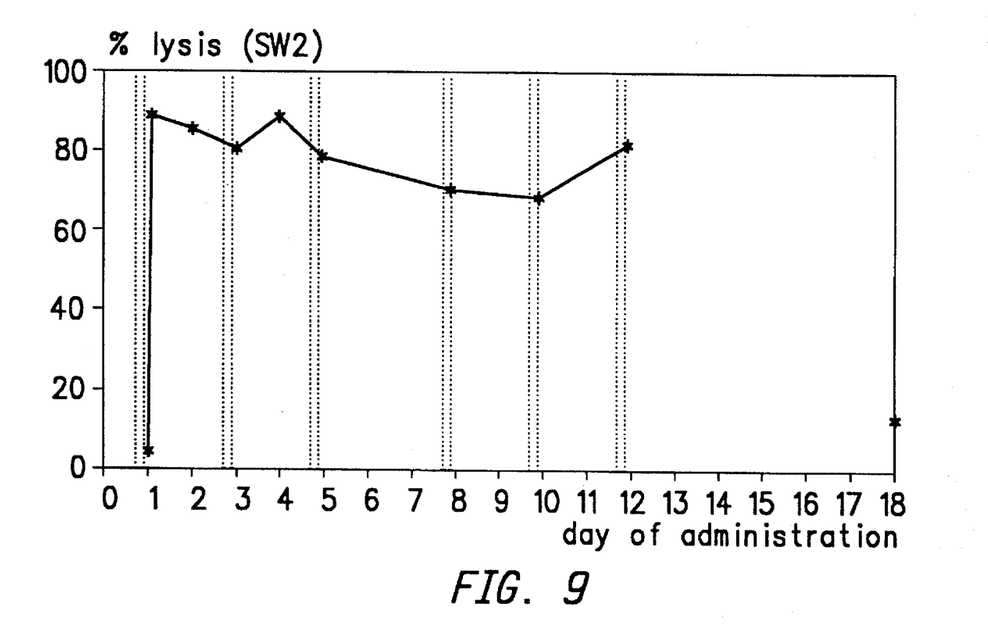
FIG. 9: Complement-dependent cytolysis (in % of lysed SW2 cells) in the serum of a SCLC patient after administration of 50 mg BR55-2/IgG3 on each of days 1, 3, 5, 8, 10 and 12. The interrupted vertical lines show the duration of infusion.

A representative result is indicated in FIG. 9 (see Example 6 for experimental details). The serum of the patients is clearly cytotoxic, in the range of 70–90% lysis for cell line SW2 over the whole duration of treatment.

The above results clearly demonstrate a biological effect of an anti-tumor antibody following administration in humans.

3.3. Human immune response against murine immunoglobulin

Since patient treatment is effected with a murine immunoglobulin, which is normally recognized as foreign by the human immune system, a human immune response against murine BR55-2 protein would be expected (human anti-mouse antibody=HAMA). Such immune response could lead to an enhanced rate of elimination of the murine antibody. Further, this mechanism can lead to neutralization of the biological activity of the antibody triggered upon activation of human effector mechanisms following the binding to the tumor cells, and result in clinical side effects.

Figure 10:
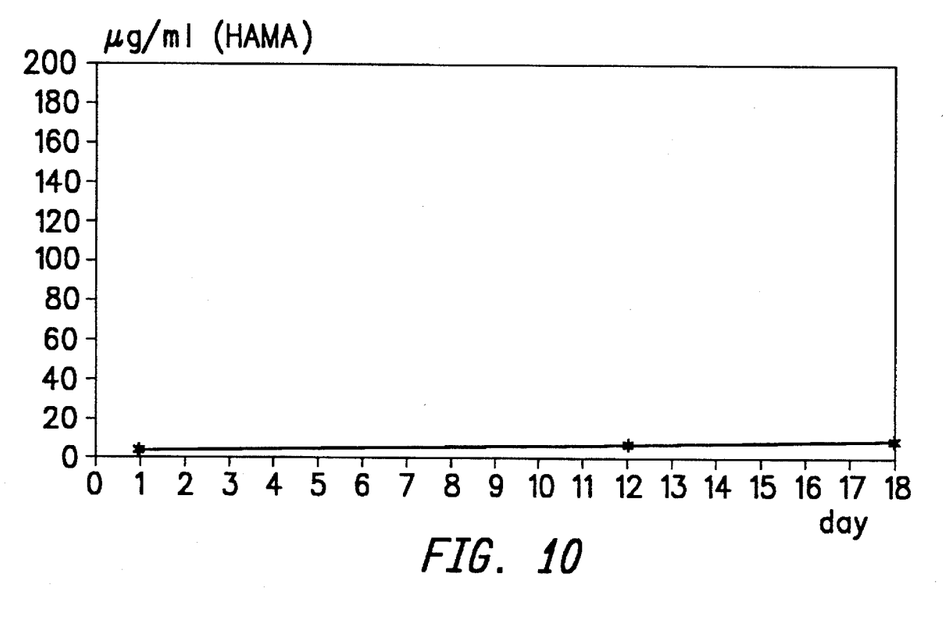
FIG. 10: Immune response against BR55-2/IgG3 in serum from a SCLC patient: HAMA titers after administration of 50 mg BR55-2/IgG3 on each of days 1, 3, 5, 8, 10 and 12.

Unexpectedly, it turns out that patients treated with BR55-2/IgG3 do not generally exhibit any pronounced immune response during and also after the period of treatment. No significant HAMA response was seen. The measured titers of anti-mouse immunoglobulin are low and not sufficient to impair or neutralize the induction of tumor cytotoxicity in serum. Further, no side effects attributable to the induction of an immune response are observed. A representative diagram showing the development of the human immune response during the course of treatment is indicated in FIG. 10 (see Example 7 for experimental details).

4. As part of a different clinical trial not involving SCLC patients, after a single dose administration of 50 mg BR55-2/IgG3 antibody, substantial lysis in vivo of tumor cells in the patients' pleural effusion fluid, ascites or bone marrow has also been found. Activation of human cell lysis can thus be demonstrated in ascites, pleural effusion fluid and bone marrow.

In view of the above experimental results monoclonal antibodies BR55-2 and fragments thereof having the specificity of BR55-2, and variants thereof, are thus useful in the treatment of SCLC.

For the above-mentioned use the dosage will, of course, vary depending upon e.g. the subject patient's age, the stage of disease, or the mode of administration, and can be determined by the specialist in each individual situation. It will also vary when the antibodies are used in combination with other chemotherapeutic agents, e.g. cytostatic agents. Administration is e.g. parenteral by injection or infusion, optionally together with effector cells, preferably leukocytes, e.g. autologous peripheral blood mononucleocytes. The dosage administered in the larger mammal is e.g. of from about 0.01 mg/m$^2$ to about 2000 mg/m$^2$. Co-administration is normally substantially contemporaneous, thus an immunomodulator is e.g. administered from about 1 to about 6 days before administration of the antibody. Injection can be e.g. subcutaneous, intramuscular, intraperitoneal, intracavital or intravenous.

Variants of BR55-2 are e.g. chimeric antibodies, humanized antibodies, class-switch variants, labelled antibodies and immunoconjugates. Fragments are e.g. Fab and F(ab')$_2$ fragments. Variants and fragments can be prepared in accordance with known methods, e.g. as described in EP 0 285 059. Labeling may e.g. be effected with a radioisotope, a drug, an immunomodulator, a biological response modifier, a lectin or a toxin.

Preferred is intact BR55-2, especially of IgG3 isotype.

In view of their property of being internalized antibodies BR55-2 are particularly suitable for targeting of toxins and radioisotopes.

The term "a monoclonal antibody BR55-2 or a fragment thereof having the specificity of monoclonal antibody BR55-2, or a variant thereof" means a monoclonal antibody, antibody fragment or antibody variant recognizing the antigen recognized by the monoclonal antibodies produced by deposited hybridomas BR55.2 (BR55-2/IgG3) and BR55.2S2a (BR-55-2/IgG2a).

These hybridomas have been deposited with the American Type Culture Collection, 12301 Parklawn Drive Rockville, Md. 20852, U.S.A., under the provisions of the Budapest Treaty, under deposit numbers ATCC HB 9324 on Feb. 17, 1987 and, respectively, ATCC HB 9347 on Mar. 10, 1987.

Antibodies BR55-2 are very well tolerated. Side effects are dependent on dosage, duration of administration and isotype of antibody administered. Following infusion of 50 mg to 100 mg BR55-2/IgG3 only moderate nausea and vomiting is observed in most patients.

Insofar as their availability or preparation is not specifically mentioned herein, the reagents and materials used in the operation of the present invention are known and available or may be prepared or equivalents thereof may be prepared in conventional manner.

Explanation of the Figures:

FIG. 5: As for FIG. 4, but for cell line H-69, with BR55-2/IgG3 and BR55-2/IgG2a.

The following Examples illustrate the invention. All temperatures are in degrees Centigrade. The abbreviations have the following meanings:
ADCC: antibody-dependent cell cytolysis
BSA: bovine serum albumin
CDC: complement-dependent cytolysis
EDTA: ethylene diamine tetraacetic acid
ELISA: enzyme-linked immunosorbent assay
FCS: fetal calf serum
HAMA: human anti-mouse antibody
PBMC: peripheral blood mononuclear cells
PBS: phosphate-buffered saline
RPMI: Roswell Park Memorial Institute
SDS: sodium dodecyl sulfate
SCLC: small cell lung carcinoma The materials referred to in the Examples are as follows:

| | |
|---|---|
| Cell lines H-69, OH-1 and SW2: | human SCLC lines (R. Waibl et al., Cancer Res. 48 [1988] 4318–4323) |
| Medium A: | RPMI 1640 + 2 g/l NaHCO$_3$ |
| | 100 U/ml Penicillin G |
| | 100 µg/ml streptomycin sulfate |
| | 4 mM glutamine |
| | 10% FCS (heat-inactivated, γ-globulin-free) |
| Ficoll-Paque: | density 1.077 ± 0.001 g/ml |
| PBS complete: | 8.0 g NaCl |
| | 0.2 g KH$_2$PO$_4$ |
| | 0.2 g KCl |
| | 1.15 g Na$_2$HPO$_4$ |
| | 0.13 g CaCl$_2$.2H$_2$O |
| | 0.1 g MgCl$_2$.6H$_2$O |
| | ad 1 l with dist. H$_2$O |
| PBS deficient: | 138.0 mM NaCl |
| | 1.5 mM KOH |
| | 2.7 mM KCl |
| | 6.5 mM Na$_2$HPO$_4$ |
| | pH 7.2 |
| Coating buffer: | 15 mM Na$_2$CO$_3$ |
| | 35 mM NaHCO$_3$ |
| | 3 mM NaN$_3$ |
| | pH 9.6 |
| Staining buffer: | 24.3 mM citric acid |
| | 51.4 mM Na$_2$HPO$_4$ |
| | pH 5.0 |
| Washing buffer: | 2% NaCl |
| | 0.2% Triton X-100 |
| | 10 × excess of 10% PBS def. |
| Na$_2$$^{51}$CrO$_4$: | 1 mCi/ml. |

EXAMPLE 1

Binding of BP-55-2 antibodies to SCLC cell lines (cell ELISA)

Microtiter plates are pretreated with poly-L-lysine hydrobromide (20–30 kD; 20 µg/ml in PBS def.; 100 µl/well; 30 minutes, room temperature) and washed twice with PBS def. (200 µl/well) and then incubated overnight at 4° with a suspension of cells of the cell line to be tested at a concentration of 4×10$^6$ cells/ml (50 µl of cell suspension/well; medium A). After centrifugation and removal of the supernatant the cells are fixed with 50 µl-glutaraldehyde (0.1% in physiological saline) per well for 5 minutes at room temperature, centrifuged, the supernatant is removed, the cells resuspended in 200 µl/well of PBS def./1% BSA/0.1% NaN$_3$ and left for 1 hour at room temperature.

After removal of the supernatants and washing twice with 200 µl PBS/Tween 20 (0.05%) per well for 1 hour at 37°, the antibody is incubated for 1 hour at 37° (coating buffer is PBS def.). About 100 µg/ml is chosen as the highest concentration for the determination of antibody binding to the test cells. Unbound antibody is washed out with 2×100 µl of ice-cold PBS/Tween 20 (0.05%) per well and peroxidase-conjugated antibody is added with a pipette. The conjugate used for the antibody assay is rabbit anti-mouse IgG-peroxidase or rabbit anti-mouse IgG-F(ab')2-peroxidase (such as the reagents of Dianova Co.) 1:1000 in PBS def./2% FCS. After incubation for 40 to 60 minutes at 37° the wells are washed thrice with the above PBS/Tween 20 solution and then 100 µl of the following substrate solution is added to each well: 40 mg o-phenylenediamine dihydrochloride, 100 ml staining buffer, 20 µl $H_2O_2$ (30%). After about 5 minutes colour development is stopped by addition of 50 µl of 4N $H_2SO_4$/well. Binding of the antibody to the cells is determined by measuring extinction at 492 nm (calibration is at 620 nm). Where non-adherent cell lines are used all washing steps are effected by cell centrifugation and resuspension.

EXAMPLE 2

Human complement-dependent cytolysis (CDC) of SCLC cell lines in vitro

On the day preceding the assay the tumor target cells are transferred into fresh medium A and kept at 37°/5% $CO_2$ in a cell culture flask.

$^{51}$Cr labelling of the target cells:

The cells are collected from the culture flask and incubated at a concentration of 2×10$^6$ to 5×10$^6$ cells in 800 µl of medium A at 37°/5% $CO_2$ for 2 hours with 100 µCi $Na_2{}^{51}CrO_4$. The cells are then washed with medium A to remove the excess $^{51}$Cr, resuspendend in fresh medium A and their concentration is adjusted to 2×10$^5$ to 3×10$^5$ cells/ml.

CDC:

100 µl aliquots of this suspension of target cells are pipetted into each well and, 50 µl aliquots of the antibody solution diluted to the desired concentration in PBS def. are added. Then 100 µl aliquots of a human complement preparation (final dilution of the complement>1:15) are added per well and the cells are incubated overnight at 37°/5% $CO_2$. The supernatants are harvested with a Skatron-Harvesting-Press and counted in a γ-counter. This yields the value for the experimental release.

For determination of total $^{51}$Cr release the cells are treated as above but with the complement preparation replaced by a solution of 2% SDS, 50 mM $Na_2CO_3$ and 10 mM EDTA. The value for spontaneous $^{51}$Cr release is obtained by replacing the complement preparation with medium A and the antibody solution with 50 µl PBS complement or NaCl 0.86%.

After counting the result is computed as follows:

$$\% \text{ lysis} = \frac{(\text{experimental release minus spontaneous release}) \times 100}{\text{total release minus spontaneous release}}$$

EXAMPLE 3

Antibody-dependent cell cytotoxicity (ADCC) for human SCLC cell lines using peripheral blood mononuclear cells (PBMCs)

On the day preceding the assay the tumor target cells are transferred into fresh medium A and kept at 37°/5% $CO_2$ in a cell culture flask.

$^{51}$Cr labelling of the target cells is effected as described in Example 2 above.

Isolation of PBMCs:

50 ml of heparinized fresh human blood are diluted with 60 ml of PBS complete containing 0.1% glucose. 15 ml aliquots of this solution are layered on top of 15 ml of Ficoll-Paque solution and the tubes are centrifuged at 400 g for 30 to 60 minutes. The plasma supernatants are discarded, the PBMC layers are collected and diluted to 50 ml with PBS complete+0.1% glucose. After centrifugation at about 80 g (10 minutes), resuspension of the pellet in 25–30 ml PBS complete+0.1% glucose, and recentrifugation (80 g, 10 minutes), the pellet is collected, suspended in medium A, the cells are counted and the suspension is diluted with medium A to about 2×10$^6$ to 9×10$^6$ cells/ml. 100 µl aliquots are pipetted into each well of a microtiter plate and the effector cells are incubated overnight at 37°/5% $CO_2$.

ADCC:

100 µl of $^{51}$Cr-labelled target cells are added to the preincubated effector cells in the desired ratio of effector cells to target cells. 50 µl of monoclonal antibody solution diluted to the desired concentration with PBS def. are added and the plate is incubated for 4 to 20 hours at 37°/5% $CO_2$. The supernatants are then harvested with a Skatron-Harvesting Press and counted in a γ-counter. This yields the value for the experimental release.

Total $^{51}$Cr release is determined as above but replacing PBMCs with 100 µl of 2% SDS, 50 mM $Na_2CO_3$ and 10 mM EDTA and replacing the antibody solution with 50 µl of PBS def. Spontaneous $^{51}$Cr release is obtained by replacing PBMCs with 100 µl of medium A and the antibody solution with 50 µl of PBS def. The result is computed as under Example 2 above.

EXAMPLE 4

Antibody-dependent cell cytotoxicity (ADCC) for SCLC cell lines using heparinized fresh human whole blood On the day preceding the assay the tumor target cells are transferred into fresh medium A and kept at 37°/5% $CO_2$ in a cell culture flask.

$^{51}$Cr labelling of the target cells is effected as described under Example 2 above.

Fresh human whole blood is diluted 1:3 with medium A and 100 µl aliquots are pipetted into the wells of a microtiter plate. 50 µl of antibody solution diluted to the desired concentration with PBS def. and 100 µl aliquots of marked target cells are added. After incubation for 4 to 20 hours at 37°/5% $CO_2$ the supernatants are harvested with a Skatron-Harvesting-Press and $^{51}$Cr-release is determined in a γ-counter (=experimental release).

For total $^{51}$Cr release determination the cells are treated with 100 µl of 2% SDS, 50 mM $Na_2CO_3$ and 10 mM EDTA, and 50 µl of PBS def. is added in place of antibody solution. Spontaneous $^{51}$Cr release is obtained by adding 100 µl of medium A and 50 µl of PBS to the target cells. The result is computed as under Example 2 above.

EXAMPLE 5

Determination of mouse-IgG3 antibody titer in patient serum (ELISA)

100 µl aliquots of a rabbit anti-mouse IgG solution are added to the wells of microtiter plates, coating buffer is added and incubation is effected at 37° for 30 to 60 minutes.

The plates are washed 6 times with washing buffer, 200 µl of PBS def./5% FCS are added, and incubation is effected for 30 minutes at 37°. The plates are washed, 100 µl aliquots of various dilutions of the serum to be assayed and of standard (BR55-2/IgG3) are added (dilutions are in PBS def./2% FCS), and the plates are incubated for 60 minutes at 37°. Unbound antibody is washed out as described above and 100 µl aliquots of peroxidase-conjugated antibody (rabbit-anti-mouse IgG3/peroxidase) are added.

After incubation for 30 minutes at 37° the plates are washed 4 times with the above washing buffer and twice with staining buffer.

100 µl aliquots of substrate solution (40 mg o-phenylenediaminedihydrochloride, 100 ml of staining buffer, 20 µl of $H_2O_2$ 30%) are added and colour development is stopped after 4 to 5 minutes with 50 µl aliquots of 4 N $H_2SO_4$. Photometric evaluation is effected by measuring extinction at 492 nm (reference measurement 620 nm), the antibody titers of the samples are read from the standard curve.

EXAMPLE 6

Ex vivo tumor cytotoxicity of sera from treated SCLC patients

On the day preceding the assay the tumor target cells (from e.g. the human SCLC cell line SW2) are transferred to fresh medium A and kept at 37°/5% $CO_2$ in a cell culture flask.

Patient serum samples are frozen and thawed only once. They are used undiluted.

100 µl aliquots are pipetted into the wells of a microtiter plate and kept at 4°, while the target cells are labelled with $^{51}Cr$ as described under Example 2 above and added to the patient sera.

After incubation overnight at 37°/5% $CO_2$ the supernatants are harvested with a Skatron-Harvesting-Press and $^{51}Cr$-release is determined in a γ-counter (=experimental release).

For total $^{51}Cr$ release determination the cells are treated with 2% SDS, 50 mM $Na_2CO_3$ and 10 mM EDTA in place of serum. Spontaneous $^{51}Cr$ release is obtained by using medium A in place of serum. The result is computed as under Example 2 above.

EXAMPLE 7

Determination of human immune response against mouse immunoglobulin (ELISA) (HAMA)

100 µl aliquots of a solution of BR55-2/IgG3 at a concentration of 10 µg/ml are transferred to the wells of microtiter plates and after addition of 200 µl/well of coating buffer and 3% gelatine incubation of the patient sera (diluted in PBS/1% gelatine) is effected at 37° for 30 to 60 minutes.

The further procedure and computation are as under Example 5 above, except that the peroxidase-conjugated antibody used is goat anti-human IgG+IgM/peroxidase, diluted in PBS/1% gelatine.

EXAMPLE 8

Expression of the Lewis Y antigen on glycoproteins of SCLC cell line SW2

Glycoproteins or plasma membranes of SW2 cells are isolated in conventional manner (D. Thom et al., *Biochem. J.* 168 [1977] 187–194). After SDS gel electrophoresis (U. K. Laemmli, *Nature* 227 [1970] 680–685) it can be shown by conventional Western blot analysis (M. B. Wilon and P. K. Nakane, *Immunofluoroscence and Related Staining Techniques*, Elsevier/North Holland Biomedical Press, Amsterdam [1978] 215–224) that antibodies BR55-2 specifically bind to glycoprotein fractions of cell line SW2.

We claim:

1. A method for the destruction of small cell lung carcinoma cells in a patient suffering from small cell lung carcinoma comprising administering to the patient (i) the monoclonal antibody produced by hybridoma ATCC HB 9324 or hybridoma ATCC HB 9347, said monoclonal antibody specifically binding to both the difucosyl blood group antigens Y-6 and B-7-2, (ii) an antigen binding fragment thereof having the specificity of said monoclonal antibody, or (iii) a variant of said monoclonal antibody or antigen binding fragment thereof having the specificity of said monoclonal antibody, in an amount effective to destroy small cell lung carcinoma cells.

2. The method of claim 1 wherein said monoclonal antibody is administered together with effector cells.

3. The method of claim 2 wherein the effector cells are autologous peripheral blood mononucleocytes.

4. The method of claim 1 wherein the amount effective to destroy small cell lung carcinoma cells is from about 50 to about 100 milligrams per day in a human patient.

5. The method of claim 1 comprising administering a variant of the monoclonal antibody which is a chimeric antibody.

6. The method of claim 1 comprising administering a variant of the monoclonal antibody which is a labelled antibody.

7. The method of claim 6 wherein the labelled antibody is labelled with a drug.

8. The method of claim 1 comprising administering a variant of the monoclonal antibody which is a humanized antibody.

9. The method of claim 1 wherein administration is parenteral.

10. The method of claim 1 wherein administration is subcutaneous, intramuscular, intracavital or intravenous.

* * * * *